May 14, 1940.
R. M. HATTON
Plant Pat. 396
ROSE PLANT
Filed July 25, 1939
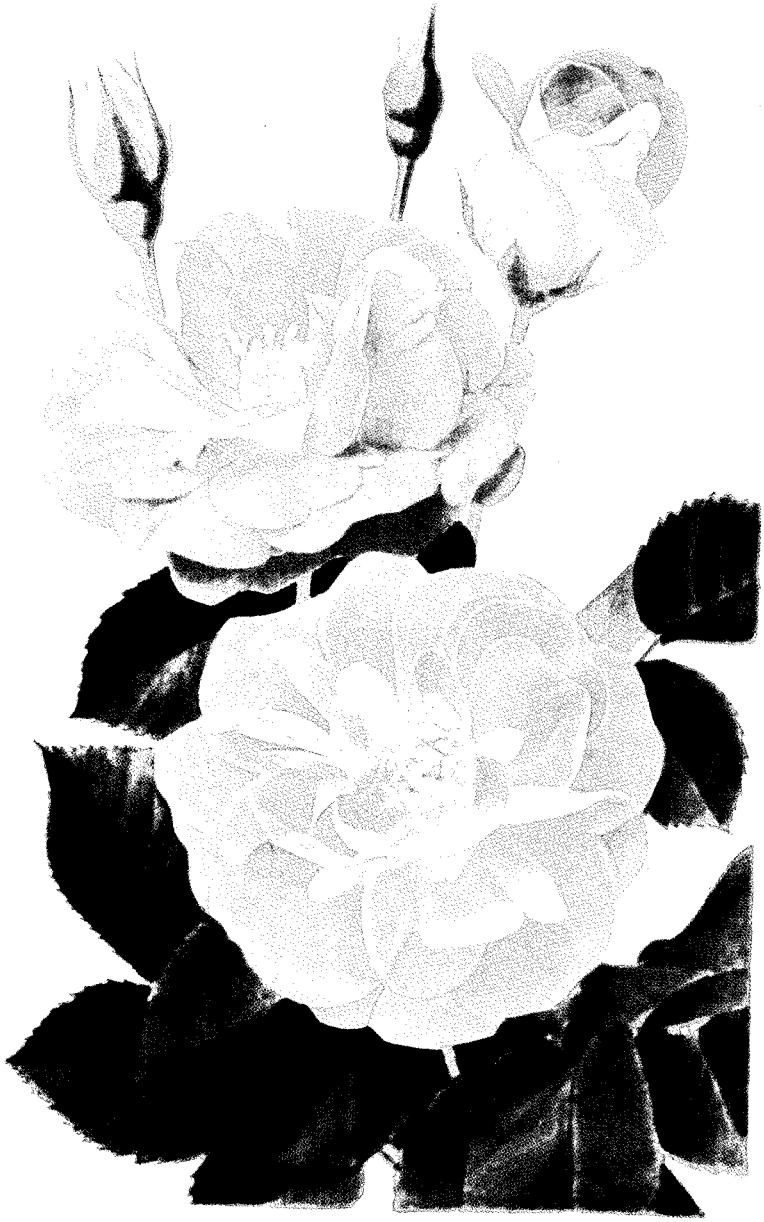
Inventor
R. M. Hatton
By Robb & Robb
attorneys Patented May 14, 1940

Plant Pat. 396

UNITED STATES PATENT OFFICE

396

ROSE PLANT

Robert Marion Hatton, Harrisburg, Pa., assignor to The Conard-Pyle Company, West Grove, Pa.

Application July 25, 1939, Serial No. 286,473

1 Claim. (Cl. 47—61)

The present invention relates to a new and distinct variety of pillar rose, the result of a definite effort to produce an improvement in this type embodying the dominating characteristics of its parents.

This new rose, actually grown from a seedling of the specific cross Rosella × Margaret McGredy, is distinctive primarily in respect to its habit of growth and its unusually interesting variation in the coloring of the foliage, both contributing to make it a bush of good shrub value.

In addition to the above-mentioned features, this new variety is notable for the extraordinary, exciting quality of vivid color contrast of its flowers when the rose is in bloom.

The following is a detailed description of this new rose, the color terminology being in accord with the 1939 Royal Horticultural Society Chart, except where otherwise the Ridgway Standard is applicable.

Type: Hardy; pillar—outdoors; seedling; for garden decoration.
Class: Hybrid.
Seedling:
*Seed parent.*—Rosella.
*Pollen parent.*—Margaret McGredy.
Propagation: It holds its distinguishing characteristics through succeeding propagations by grafting and by budding.

*Flower*

Locality where grown: West Grove, Pennsylvania.
Flowers borne: Single—several to stem; on strong, medium stems.
Quantity of bloom: Free—outdoors.
Continuity: One season.
Fragrance: Slight; fruity.
Bud:
*Peduncle.*—Short; medium slender; medium heavy—Light Elm Green (Ridgway, Plate XVII); medium rough—few Elm Green prickles.
*Before calyx breaks.*—Size—medium. Form—globular; with appendages on the surface of the bud; with slender, foliaceous parts extending beyond the tip of the bud equal to ¼ of its length.
*As first petals open.*—Size—medium. Form—globular.
*Color.*—Outside face—Vermilion edge (P18–18) shading to Canary Yellow (P2–2) base. Inside—Turkey Red (P94–721) with Canary Yellow (P2–2) base.
*Opening.*—Opens up well.

Bloom:
*Size when fully open.*—Medium, 3 inches to 3½ inches.
*Petalage.*—Semi-double (2 or even 3 rows) 15 to 20 petals.
*Form.*—Flat—open at first; becoming open; petals remaining at first outward; becoming later very loosely rolled outward.
Petals: Thick; outside—shiny; with inside velvety.
*Shape.*—Round.
The following description of a newly opened flower was made from a rose grown outdoors May 31, 1939, at Jennersville, Pennsylvania.
*Color.*—Outside petal; outside surface—Vermilion edge (P18–18) shading to Canary Yellow (P2–2) base; inside surface—Turkey Red (P94–721), Canary Yellow (P2–2) base. Intermediate petal—same as outside petal.
*General color effect.*—Newly opened flower; face—Vivid Turkey Red (P94–721), with a large Canary Yellow (P2–2) zone around the stamens; reverse—Vermilion edge (P18–18) shading to Canary Yellow (P2–2) base. Three days open—Magenta (P27–27).
*Behavior.*—Drop off cleanly.

*Reproductive organs*

Stamens: Medium; arranged regularly, mixed with petaloids.
Filaments: Medium Primuline Yellow (Ridgway, Plate XVI), with anthers.
Anthers: Small.
Pollen: Antimony Yellow (Ridgway, Plate XV).
Styles: Medium.

*Fruit*

No fruit observed as yet.

*Plant*

Foliage:
*Leaves.*—Compound of 5, 7 leaflets; abundant; medium heavy, leathery, glossy.
*Leaflets.*—Oval, with apex mucronate; base round; margin serrate.
*Color.*—Mature; upper surface, normal—Hellebore Green (Ridgway, Plate XVII); under surface—Biscay Green (Ridgway, Plate XVII). Young; upper surface—Light Hellebore Green (Ridgway, Plate XVII), edged Mahogany Red (Ridgway, Plate II); under surface—Warbler Green (Ridgway, Plate IV) suffused Garnet Brown (Ridgway, Plate I).

*Rachis (the supporting stem of the compound leaf).*—Medium. Upper side—grooved, hairy. Under side—extremely prickly—thorny.

*Stipules.*—Medium long, medium wide, with long points, turning out at an angle of more than 45°.

*Disease.*—Resistant to mildew—blackspot.

Growth:

*Habit.*—Upright, much branched—about eight feet.

*Growth.*—Free.

*Canes.*—Heavy.

*Main stems.*—Brown. Thorns—several, long, hooked downward; with short narrow base. Prickles—none. Hairs—none.

*Branches.*—Red. Thorns—several; long, hooked downward; with short, narrow base. Prickles—none. Hairs—none.

*New shoots.*—Red. Thorns—several; long, hooked downward; long narrow base. Prickles—none. Hairs—none.

I claim.

A new and distinct variety of rose plant of the pillar type characterized as to novelty by its distinctive habit of growth, the color variation of its foliage, and vivid color contrast of its flowers, substantially as shown and described.

R. MARION HATTON.